United States Patent [19]
Gieringer

[11] Patent Number: 5,584,839
[45] Date of Patent: Dec. 17, 1996

[54] INTRAARTICULAR DRILL GUIDE AND ARTHROSCOPIC METHODS

[76] Inventor: Robert E. Gieringer, P.O. Box 113034, Anchorage, Ak. 99511

[21] Appl. No.: 355,404

[22] Filed: Dec. 12, 1994

[51] Int. Cl.$^6$ ............................ A61B 17/17; A61B 17/56
[52] U.S. Cl. ................................ 606/96; 106/103
[58] Field of Search ............................ 606/96, 97, 98, 606/102, 103, 104, 86, 87, 88

[56] References Cited

U.S. PATENT DOCUMENTS

| | | | |
|---|---|---|---|
| 2,181,746 | 11/1939 | Siebandt | 606/98 |
| 3,867,932 | 2/1975 | Huene | 606/96 |
| 4,444,180 | 4/1984 | Schneider et al. | |
| 4,708,139 | 11/1987 | Dunbar, IV | |
| 4,739,751 | 4/1988 | Sapega et al. | |
| 4,744,353 | 5/1988 | McFarland | |
| 4,813,407 | 3/1989 | Vogen | |
| 4,862,882 | 9/1989 | Venturi et al. | 606/96 |
| 4,920,958 | 5/1990 | Walt et al. | 606/103 |
| 5,030,219 | 7/1991 | Matsen, III et al. | 606/86 |
| 5,112,336 | 5/1992 | Krevolin et al. | 606/96 |
| 5,154,720 | 10/1992 | Trott et al. | 606/96 |
| 5,269,786 | 12/1993 | Morgan | 606/96 |
| 5,312,412 | 5/1994 | Whipple | 606/96 |
| 5,320,115 | 6/1994 | Kenna | 128/898 |

FOREIGN PATENT DOCUMENTS

0591985A1  4/1994  European Pat. Off.

OTHER PUBLICATIONS

"Surgical Techniques–Bankart repair: A new arthroscopic technique", Neil J. Maki, M. D., AAOS Annual Meeting, Feb. 1990.
"Surgical Techniques–Arthroscopic Bankart suturing yields better external rotation", Bill Edelman.
"Arthroscopic Labral Repair tot he Glenoid Rim", Douglas T. Harryman II, M. D. et al., Arthroscopy: The Journal of Arthorscopic and Related Surgery, 10(1):20–30, 1994.
"Arthroscopic Transglenoid Bankart Suture Repair", Craig D. Morgan, M. D., Operative Techniques in Orthopaedics, vol. 1, No. 2 (Apr.), 1991: pp. 171–179.
"Arthroscopic reconstruction for anterior shoulder instability", Richard B. Caspari, M. D., Techniques orthop 1988:3(1):59–66, 1988.
"Arthroscopis Bankart Suture Repair: Technique and Early Results", Craig D. Morgan et al., Arthroscopy: The Journal of Arthroscopic and Related Surgery, 3(2):111–122, 1987.
"Technique for Arthroscopic Suture Capsulorrhaphy for Anterior Shoulder Instability", Acufex Microsurgical, Inc., 1989.
"Pinn.ACL™ Guide System", 1994 Product Catalog, Linvatec, p. 66.

Primary Examiner—Michael Powell Buiz
Assistant Examiner—Scott B. Markow
Attorney, Agent, or Firm—Bromberg & Sunstein

[57] ABSTRACT

An intraarticular drill guide having a cannulated guide shaft and a sliding shaft mounted for both reciprocal movement and axial rotation. A hook attached to the distal end of the sliding shaft is provided for locating against a bone positioned between it and the cannulated guide shaft. The drill guide has a handle for pulling back on the sliding shaft to force the tip of the hook into the far side of the bone.

The method of the invention involves pressing the cannulated guide shaft against a bone through an arthroscopic portal. The sliding shaft with a hook at its end is inserted into the joint. Pulling back on the sliding shaft holds the bone between the hook and the cannulated guide shaft. A drill is operated through the cannulated guide shaft. A tissue repair is completed in accordance with the invention by passing suture ends through the tunnel that is drilled and tying them about a button anchor. The button anchor of the invention is bioabsorbable made from polyglactic acid.

23 Claims, 3 Drawing Sheets

5,584,839

INTRAARTICULAR DRILL GUIDE AND ARTHROSCOPIC METHODS

BACKGROUND OF THE INVENTION

The present invention relates to arthroscopic tissue repairs such as rotator cuff repairs, Bankart repairs and capsulorrhaphy. In particular, the present invention relates to an intraarticular drill guide for use in performing such repairs.

Surgeons have long recognized the advantages of arthroscopic repairs over the traditional open surgical repair. An open repair requires a relatively large incision which raises the prospect of complications due to restriction of shoulder motion, pain, risk of infection, length of hospital stay and cosmesis (small scars). Arthroscopic surgery is performed through small incisions or holes which permit elongated instruments to enter the joint being operated upon. An arthroscope is used through one of these holes into the joint to permit visualization, while other holes are used for the instruments to enter the joint.

In performing a tissue repair, it is often necessary to anchor tissue to a bone. There are many techniques which use items such as metal anchors, tacks or staples to secure tissue to bone. Such items can cause damage to a joint if they were to break loose. Therefore, alternative methods using sutures to secure tissue to bone are appealing. A suturing method for capsule repair is described in Caspari, R. B., "Arthroscopic Reconstruction for Anterior Shoulder Instability," *Techniques in Orthopedics* 3(1) 59–66, 1988, the disclosure of which is hereby incorporated by reference herein. A suture punch is used to place the sutures about the tissue to be affixed to the bone. Caspari drills a hole from the front side of the bone at the site of the tissue repair. The Caspari arthroscopic drill guide is affixed against the bone only on the front side. The lack of control over the exit hole of the drill present a risk of injury to neurovascular structures. The technique requires that sutures be tied over a muscle. This limits muscle function and requires that permanent sutures be avoided. Instead, absorbable sutures last only for a few weeks and thus do not allow as strong a repair. In an open surgery, sutures can be used to hold down the repaired tissue against the bone without wrapping over adjoining muscle such that non-absorbable permanent sutures may be used.

Harryman II, D. T. et al., "Arthroscopic Labral Repair to the Glenoid", *Arthroscopy*, Vol. 10, No. 1, pp. 20–30, 1994, discloses a technique that may be used for Bankart repairs but not rotator cuff or capsulorrhaphy. An arthroscopic intraarticular drill guide is shown for drilling a hole across a corner of a bone. The technique is difficult to perform.

SUMMARY OF THE INVENTION

The present invention is directed to an intraarticular drill guide with both front and back localization for the drill hole to avoid injury to surrounding tissues. The drill guide has a cannulated guide shaft and a sliding shaft. A hook attached to the distal end of the sliding shaft is used for localization at the far end of the hole. The sliding shaft can be pulled or retracted to force the tip of the hook in the direction of the distal end of the cannulated guide shaft to hold the bone therebetween. The sliding shaft is also axially rotatable so as to be able to swing the hook out from behind the bone permitting the sliding shaft to be retracted out from the joint. The drill guide including the cannulated guide shaft and the sliding shaft with its hook at its distal end are all insertable through an arthroscopic portal into a joint. At the proximal end of the cannulated guide shaft, means are provided for being able to pull the sliding shaft back towards the cannulated guide shaft to force the hook at the end of the shaft into the far side of the bone.

In accordance with a method of the invention, a cannulated guide shaft and a sliding shaft are passed through an arthroscopic portal. Upon extending beyond the far side of the bone, the sliding shaft is pulled back to hold the bone between the hook at the end of the sliding shaft and the cannulated guide shaft. A drill is operated through the cannulated guide shaft to drill a hole through the bone. A sliding shaft with a hook at its end may need to be rotated as it is inserted or removed from behind the bone. Having drilled the hole through the bone, a suture separately placed may be extended around the tissue to be anchored to the bone. Both ends of the suture are pulled back through the bone tunnel. The sutures need to be secured to the bone at the opposite end of the tunnel. In accordance with an embodiment of the invention, the sutures are inserted through the holes of a button greater in size than the opening of the tunnel and tied together so as to hold the repaired tissue against one end of the tunnel and the button against the other end of the tunnel. The button is preferably made of a bioabsorbable material such as polyglactic acid.

The drill guide of the invention permits drilling of a hole in the bone with substantially reduced risk to surrounding tissues. A strong repair can be effected with nonabsorbable sutures firmly secured within a tunnel through the bone. The drill guide is advantageously used intraarticularly.

Other objects and advantages of the invention shall become apparent during the following description of the presently preferred embodiments of the invention taken in conjunction of the drawings.

DETAILED DESCRIPTION OF THE PREFERRED EMBODIMENTS

Figure 1:
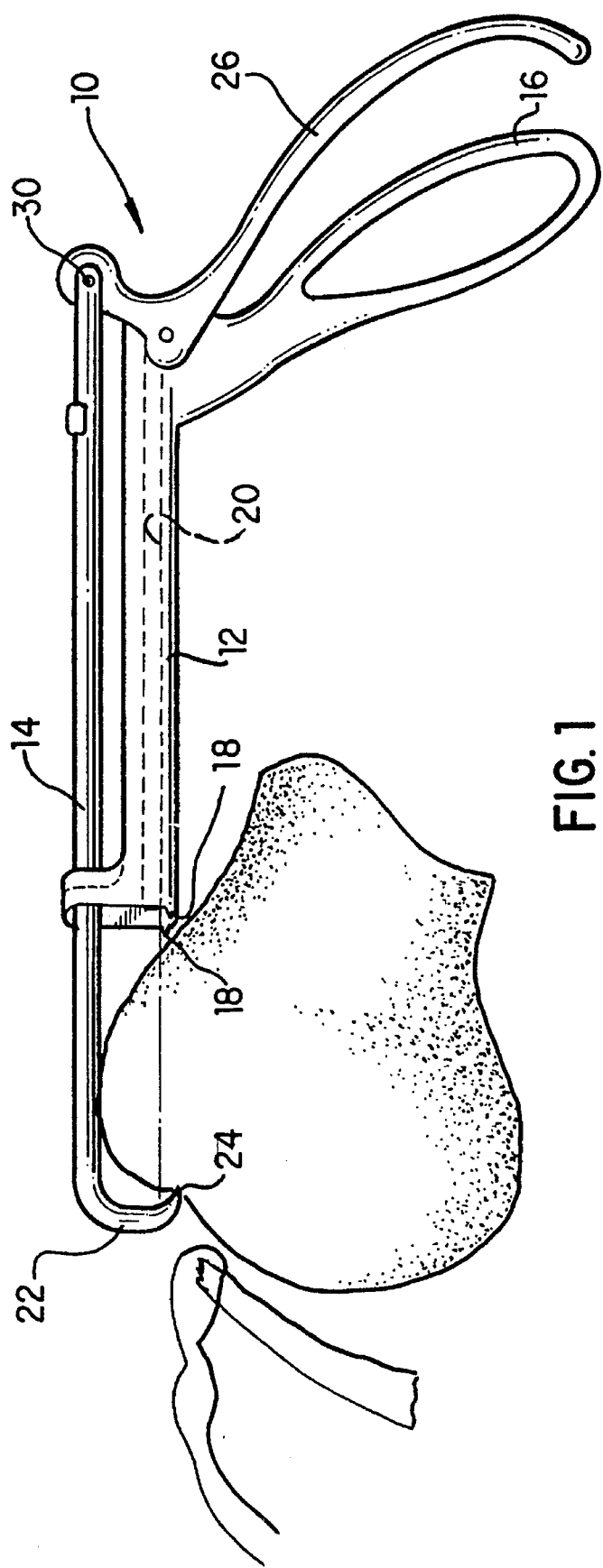
FIG. 1 is an isometric view of an intraarticular drill guide of the invention in use in the repair of a rotator cuff injury.
Figure 2:
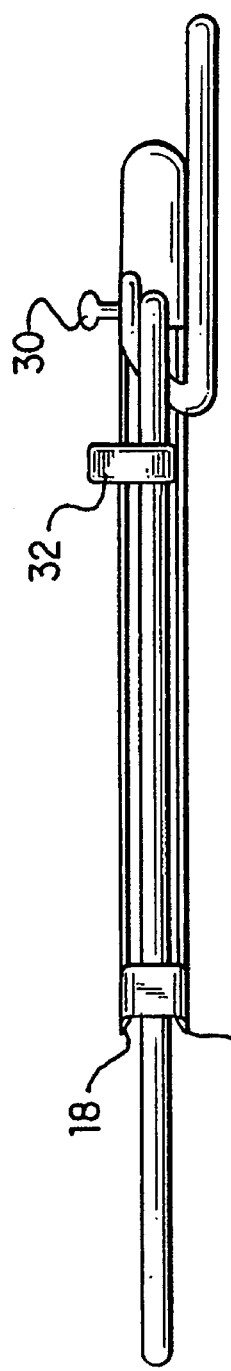
FIG. 2 is a top view of the intraarticular drill guide of FIG. 1.

An intraarticular drill guide 10 of an embodiment of the invention is shown in FIG. 1. The drill includes a cannulated drive shaft 12 and a sliding shaft 14. A hand grip 16 extends from the proximal end of the cannulated drill shaft 12 for use as part of the handle of the drill guide 10. The distal end of the cannulated guide shaft may be provided with one or more spikes 18 for assisting in firmly securing the drill guide shaft in place against a bone to be drilled. The longitudinal cannulation 20 extending through the guide shaft 12 has a presently preferred diameter of 2.2 mm. and length of 8 cm.

It is designed to allow passage for a 2 mm. drill or suture retriever. The sliding shaft 14 has a hook at its distal end. A tip 24 of the hook points back towards the cannulated guide shaft. The shaft 14 is mounted on the cannulated guide shaft for reciprocal movement of the tip 24 toward and away from the cannulated guide shaft. The sliding shaft 14 moves parallel to the axis of the cannulation 20. In accordance with a presently preferred embodiment, the axis of the sliding shaft 14 is mounted about 5 mm. from the axis of the cannulation 20. The sliding shaft 14 and the cannulation 20 must be close enough together so as to permit the sliding shaft to be inserted through an arthroscopic portal. The tip 24 of the hook and the spikes 18 are opposed to one another for holding a bone therebetween.

The proximal end of the sliding shaft 14 is attached to a lever 26 that forms a part of the drill guide handle. The lever 26 has a fulcrum formed by a pivot pin attachment to the proximal end of the cannulated guide shaft 12. A long portion of the lever 26 serves as a gripper arm. In accordance with a presently preferred embodiment, gripping the lever 26 permits controlling reciprocal movement of the sliding shaft 14 such that the tip of the hook travels in a range between 20–35 mm. from the end of the cannulated guide shaft. A shorter lever arm is attached at its end to the sliding shaft 14 by a removable pivot pin 30. Upon removing the pivot pin 30, the sliding shaft 14 may be rotated about its axis. A fixed lever arm 32 extending away from the sliding shaft 14 provides a handle for turning the sliding shaft about its axis. Alternative methods within the scope of the present invention for attaching the sliding shaft to the handle to permit reciprocal and rotational motion are known to those of ordinary skill in the art. For example, instead of the removable pin, a ball joint attachment that permits rotation may be provided between the sliding shaft and the handle.

Figure 3:
FIG. 3 is a broken drawing of an alternate embodiment of a sliding shaft for use on the intraarticular drill guide of FIG. 1.

In accordance with an alternate embodiment of the invention, more than one tip may be extended from the hook 22 of the sliding shaft 14. The distal portion of a sliding shaft of the alternate embodiment is shown at FIG. 3. The double tipped hook may provide more secure fixation at the far side of the bone. A single tip hook, on the other hand, allows use in a tighter space.

To use the guide shaft of FIG. 1, the removable pin 30 is removed to permit turning the sliding shaft 14 about its axis so that the hook 22 does not interfere with inserting the sliding shaft through the arthroscopic portal and into the joint. The drill guide is inserted into the portal through a cannula that acts as a sheath to protect the surrounding tissue. When the hook 22 is behind the bone, the sliding shaft 14 can be rotated back and the removable pin 30 reinserted to attach the sliding shaft to the handle. The bone shown in FIG. 1 is the greater tuberosity of the humerus through which a hole will be drilled during a suture repair of a rotator cuff. Sutures are used to affix the torn rotator cuff to the humerus. A surgeon's fingers are inserted through the hand grip 16. The surgeon's palm is used to push the lever arm 26 towards the hand grip 16 to pull the sliding shaft 14 back towards the cannulated guide shaft with the tip 24 of the hook 22 digging into the far side of the bone and the spikes 18 at the distal end of the cannulated guide shaft digging into the near side of the bone. A drill is then inserted through the cannulation 20 to drill a hole through the bone. After the hole has been drilled, the removable pin 30 is removed again so that the sliding shaft 14 can be rotated and then retracted from the joint. Rotating the sliding shaft 14 removes the hook out from behind the bone.

Those of ordinary skill in the mechanical art may substitute other mechanisms within the scope of the present invention for pulling back on the sliding shaft instead of the lever arm 26. For example, the proximal end of the sliding shaft may be threaded and fit through an eyelet protruding up from the proximal end of the cannulated guide shaft. A thumb screw is screwed onto the end of the threaded shaft. The screw can be tightened down to butt up against the eyelet. Further tightening pulls back on the sliding shaft. Alternatively, the sliding shaft may be provided with a ratchet mechanism which when engaged prevents the shaft from extending out further from the drill guide but permits the user to retract the sliding shaft to dig it into the far side of the bone.

Figures 4, 5:
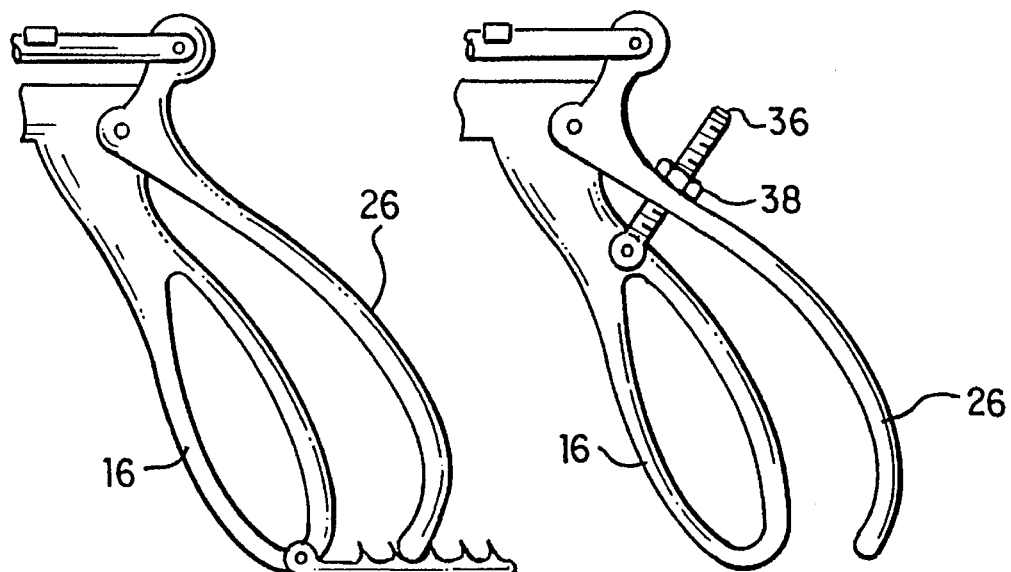
FIG. 4 is a side view of a handle of an alternate embodiment of the drill guide.
FIG. 5 is a side view of a handle of a further alternate embodiment of the drill guide.
Figure 6:
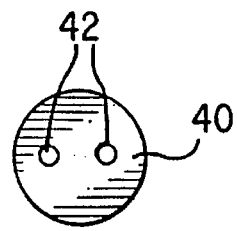
FIG. 6 is a plan view of a button anchor.

The alternative pulling mechanisms described above have an added advantage of maintaining a hold on the sliding shaft and preventing the shaft from moving out from the drill guide. A holding mechanism can be added to the lever arm 26 to permit the surgeon to release the hand grip once a bone is secured between the tip 24 of the hook and the cannulated guide shaft. Such holding mechanisms are illustrated in FIGS. 4 and 5. In the embodiment of FIG. 4, a ratchet 34 is hingedly attached to the hand grip 16. The ratchet 34 provides a series of notches, any of which may be engaged with the lever arm to prevent the lever arm from releasing the hold of the sliding shaft against the bone. The sliding shaft is released by disengaging the ratchet 34. An alternate lever holding mechanism is shown in FIG. 5. A threaded shaft 36 extends from the hand grip 16. The shaft 36 protrudes through an opening in the lever arm 26. A thumb nut 38 screws onto the shaft 36 and butts against the lever arm. When tightened, the thumb nut 38 prevents the lever arm from releasing the hold of the sliding shaft against the bone.

Figure 7:
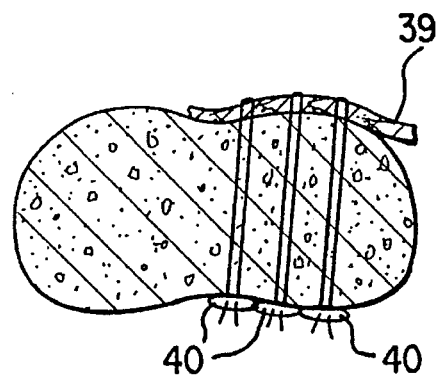
FIG. 7 is a cross-sectional view of a tissue repair of the present invention.

FIG. 7 shows a ligament 39 or other tissue to be attached to a bone with the assistance of the drill guide 10. The drill guide 10 may be used as shown in FIG. 1 for performing a rotator cuff repair and attaching a torn rotator cuff to the greater tuberosity of the humerus. Also, the drill guide 10 may be used in performing a capsulorrhaphy which attaches a capsule ligament to the glenoid or a Bankart repair which requires affixing a labrum to the glenoid. Those skilled in surgical methods will contemplate other examples of repairs within the scope of the present invention that may incorporate use of the drill guide and drilling method of the present invention.

An embodiment of a method of the present invention for drilling a hole through a bone shall now be described. An arthroscopic portal is formed through the skin at the opposite side of the bone from the ligament 39. A cannula shorter than the cannulated guide shaft is inserted through the portal. An arthroscopic cannula for use with the drill guide is about 7 mm. in diameter or slightly larger if necessary. The sliding shaft and cannulated guide shaft of the drill guide 10 are inserted through the cannula. The intraarticular drill guide 10 can locate the exit end and entrance of the hole to be drilled. Either end may be located first. The sliding shaft 14 is inserted into the joint using the hook 22 to locate the exit end of the hole near the ligament. The ligament 39 is detached from the bone either due to injury or surgical detachment and is usually out of the way of the device. If necessary, it can be pushed aside with the distal end of the sliding shaft. The cannulated guide shaft 12 is pressed against the bone at the entrance of the hole to be drilled. The drill guide may include spikes 18 to secure the cannulated guide shaft in proper position. Once both ends of the hole have been located, a drilling pin is inserted through the cannulated guide shaft and drilled through the bone. The drill pin typically drills a 2 mm. diameter tunnel.

After drilling the hole through the bone in accordance with the invention, a suture is placed into a ligament in a standard manner, using a Caspari suture punch, for example. A suture retriever is passed through the bone tunnel from the side of the bone near the ligament to retrieve the sutures and pull them through the hole. A permanent nonabsorbable suture may be used in accordance with this invention. The sutures can be secured by use of a button anchor 40 of the present invention. The button anchor is a disk with a pair of holes 42 therethrough. The presently preferred button anchor is bioabsorbable and made from polyglactic acid. The button anchor should be greater than 2 mm. in diameter to fit over the end of a tunnel without being able to be pulled through. The two ends of a suture are each inserted through one of the holes in the button anchor 40 and then the suture is securely tied together over the button. A tissue repair as shown in FIG. 7 is the result. Advantageously, the sutures are only tied over the ligament to be attached to the bone, leaving surrounding tissues substantially unaffected by the sutures. Several similar suture attachments may be provided through the bone to secure the tissue to the bone at several places.

An alternative fixation instead of using the button anchor 40 is to tie the sutures over the bone itself. By using two tunnels through the bone, one lead of the suture can proceed through one tunnel while the other lead of the suture goes through the other tunnel. The ends of the suture can be tied together at the opposite side of the bone.

Figure 8:
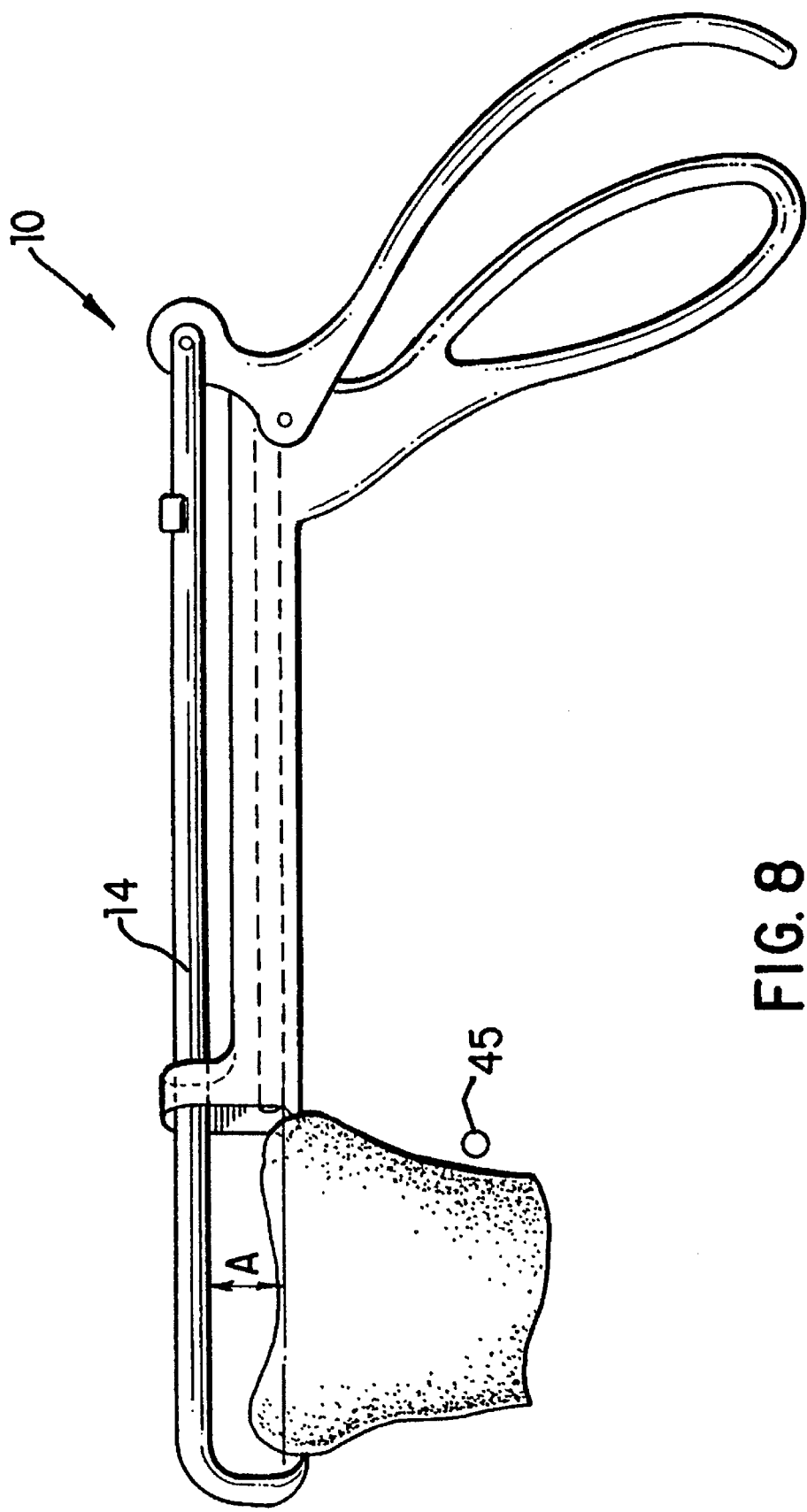
FIG. 8 is an isometric view of an intraarticular drill guide of the invention in use in the capsular or labral repair.

FIG. 8 shows the intraarticular drill guide of the present invention arranged for drilling a drill hole for a Bankart or capsule repair. Standard arthroscopic portals are used. The guide 10 directs a hole to be drilled straight across the glenoid bone. The sliding shaft 14 of the drill guide is advantageously separated by about 5 mm. from the cannulation of the drill guide. This is advantageously sufficiently small to avoid contact with the suprascapular nerve, the position of which is shown by a dot 45 in the drawing. The distance between the sliding shaft 14 and the drill guide cannulation is also large enough to drill a hole beneath the surface of the glenoid bone without breaking through the concavity of the bone in the joint. The repair is completed as described above with respect to FIG. 7.

Of course, it should be understood that various changes and modifications to the preferred embodiments described above will be apparent to those skilled in the art. For example, the sliding shaft can be removable from the cannulated guide shaft for insertion into the joint. The sliding shaft can be secured or mounted to the cannulated guide shaft once it has been inserted into the joint. Alternatively, the sliding shaft can be permanently attached to the cannulated guide shaft by a universal joint that permits rotation and reciprocal movement. These and other changes can be made without disparting from the spirit and scope of the invention and without diminishing its attendant advantages. It is therefore intended that such changes and modifications be covered by the following claims.

I claim:

1. An intraarticular drill guide comprising:

a cannulated guide shaft having a distal end and a proximal end;

a sliding shaft defining a longitudinal axis and being mounted to said guide shaft for reciprocal movement along said guide shaft into or out of a joint;

a hook attached to a distal end of said sliding shaft having a tip pointing back toward said guide shaft; and means for pulling said sliding shaft to force the tip of said hook toward the distal end of said guide shaft to hold onto a bone therebetween;

said sliding shaft being axially rotatable independent of the pulling means and said guide shaft about the longitudinal axis, so as to swing the hook out from behind the bone and permit said sliding shaft to be retracted out from the joint.

2. The drill guide of claim 1 wherein said pulling means comprises a handle attached to said guide shaft and a lever detachably connected to said sliding shaft and hingedly attached with respect to the handle.

3. The drill guide of claim 1 further comprising a tip extending from the distal end of said guide shaft for holding the bone opposite from said hook.

4. The drill guide of claim 1 wherein said hook comprises a pair of hooks each having a tip pointing back toward said guide shaft.

5. The drill guide of claim 1 further comprising on said sliding shaft, a projection extending away from said sliding shaft to assist in rotating said shaft.

6. The drill guide of claim 1 wherein said sliding shaft is mounted parallel to the cannulation and close enough to the guide shaft so that both shafts of the drill guide can be inserted together through an arthroscopic cannula.

7. An intraarticular drill guide comprising:

an elongated base member having a longitudinal passage therethrough;

a tip extending from said base member proximate an end of the longitudinal passage;

a hook having a shaft defining a longitudinal axis alongside said longitudinal passage and adjustably mounted to said base member for reciprocal movement longitudinally with respect to said base member; and means for axially rotating said shaft about the longitudinal axis to rotate said hook into or out of opposition with said tip.

8. The drill guide of claim 7 wherein reciprocal movement of said hook is provided by means for pulling said hook toward said tip.

9. The drill guide of claim 8 wherein said pulling means comprises a handle attached to said base member and a lever detachably connected to said hook and hingedly attached with respect to the handle.

10. The drill guide of claim 7 wherein said hook has a pair of tips pointing back toward said base member.

11. The drill guide of claim 7 wherein said rotating means comprises a grip attached to said hook that can be easily grasped for rotating said hook.

12. An intraarticular drill guide comprising:

a cannulated guide shaft having a distal end, a proximal end, and a longitudinal cannulation between the distal end and the proximal end;

a sliding shaft defining a longitudinal axis and being mountable on said guide shaft for reciprocal movement longitudinally with respect to said guide shaft and having a distal end extending beyond the distal end of said guide shaft;

a hook extending from the distal end of said sliding shaft, said hook and sliding shaft being insertable through an arthroscopic portal into a joint; and a handle attached to the proximal end of said guide shaft including pulling means for pulling said sliding shaft to force said hook toward said cannulated guide shaft;

said sliding shaft being rotatable about the longitudinal axis for swinging said hook into or out of opposition with the distal end of said guide shaft.

13. The drill guide of claim 12 wherein said pulling means comprises a lever detachably connected to said sliding shaft and hingedly attached with respect to the handle.

14. The drill guide of claim 12 further comprising a tip extending from the distal end of said guide shaft for locating against a bone situated between said guide shaft and said hook.

15. The drill guide of claim 12 wherein said hook comprises a pair of hooks each having a tip pointing back toward said guide shaft.

16. The drill guide of claim 12 further comprising on said sliding shaft, a projection extending away from said sliding shaft to assist in rotating said shaft.

17. The drill guide of claim 12 wherein said sliding shaft is mounted parallel to the cannulation such that a distance between said sliding shaft and the cannulation is about 5 mm.

18. The drill guide of claim 12 wherein said sliding shaft is mounted close enough to said guide shaft so that both shafts of the drill guide can be inserted together through an arthroscopic cannula.

19. A method for arthroscopic drilling through a bone comprising the steps of:

forming an arthroscopic portal;

providing a cannulated guide shaft;

providing a sliding shaft alongside said guide shaft, the sliding shaft defining a longitudinal axis and having a hook at its distal end;

passing said cannulated guide shaft through the portal and against one side of the bone;

inserting said sliding shaft into the joint;

rotating said sliding shaft independent of said guide shaft about the longitudinal axis, so as to move an end top of said hook into axial alignment with said cannulated guide shaft and against an opposite side of the bone;

pulling on the sliding shaft back toward the cannulated guide shaft to hold the bone between the hook and the cannulated guide shaft; and operating a drill through the cannulated guide shaft.

20. The method of claim 19 wherein the step of inserting includes inserting the sliding shaft into the joint parallel to the cannulated guide shaft.

21. The method of claim 19 further comprising, after the step of operating the step of rotating the sliding shaft about the longitudinal axis so as to remove the hook out from behind the bone and then sliding the sliding shaft out of the joint.

22. An intraarticular drill guide comprising:

a cannulated guide shaft having a distal end and a proximal end;

a sliding shaft defining a longitudinal axis and being mountable on said guide shaft for reciprocal movement longitudinally with respect to said guide shaft and having a distal end extending beyond the distal end of said guide shaft;

a hook extending from the distal end of said sliding shaft, said hook and sliding shaft being insertable through an arthroscopic portal into a joint; and a handle attached to the proximal end of said guide shaft including pulling means which upon being pushed in a first direction toward the distal end of said guide shaft pulls and sliding shaft in an opposite direction to force said hook toward the distal end of said cannulated guide shaft said sliding shaft being rotatable about the longitudinal axis for swinging said hook into and out of opposition with the distal end of the guide shaft.

23. A method for arthroscopic drilling through a bone comprising the steps of:

forming an arthroscopic portal;

providing a sliding shaft having a hook at its distal end;

providing a cannulated guide shaft having at its proximal end means for reciprocally moving said sliding shaft along said guide shaft;

passing said cannulated guide shaft and said sliding shaft through the portal;

locating said cannulated guide shaft against the bone;

rotating said sliding shaft independent of said guide shaft about the longitudinal axis, so as to move an end tip of said hook into axial alignment with said cannulated guide shaft and against an opposite side of bone;

pushing on the moving means in one direction so as to pull the sliding shaft in an opposite direction back toward said cannulated guide shaft to hold the bone between the hook and said cannulated guide shaft; and operating a drill through the cannulated guide shaft.

* * * * *

UNITED STATES PATENT AND TRADEMARK OFFICE
CERTIFICATE OF CORRECTION

PATENT NO. : 5,584,839
DATED : December 17, 1996
INVENTOR(S) : Gieringer

It is certified that error appears in the above-identified patent and that said Letters Patent is hereby corrected as shown below:

In Column 7, Line 31:   "top" should be --tip--

Signed and Sealed this

Seventeenth Day of June, 1997

Attest:

BRUCE LEHMAN

Attesting Officer

Commissioner of Patents and Trademarks